United States Patent [19]

Miyamae

[11] Patent Number: 4,510,943

[45] Date of Patent: Apr. 16, 1985

[54] DISPLAY INHIBITION IN AN ELECTRONIC SPHYGMOMANOMETER

[75] Inventor: Ryuichi Miyamae, Osaka, Japan

[73] Assignee: Sharp Kabushiki Kaisha, Osaka, Japan

[21] Appl. No.: 468,882

[22] Filed: Feb. 23, 1983

[30] Foreign Application Priority Data

Feb. 24, 1982 [JP] Japan .............................. 57-26430[U]

[51] Int. Cl.³ .............................................. A61B 5/02
[52] U.S. Cl. ...................................... 128/680; 128/709
[58] Field of Search ......................... 128/677, 680-683, 128/687, 689, 701-702, 705-707, 709-710, 715, 773; 381/51, 53; 340/573

[56] References Cited

U.S. PATENT DOCUMENTS

| | | | |
|---|---|---|---|
| 3,732,868 | 5/1973 | Willems et al. ..................... | 381/51 X |
| 3,830,227 | 8/1974 | Green .................................. | 128/701 |
| 3,986,498 | 10/1976 | Lewis ............................... | 128/706 X |
| 4,083,366 | 4/1978 | Gombrich et al. ............. | 128/706 X |
| 4,326,536 | 4/1982 | Kitagawa et al. ................. | 128/682 |
| 4,431,866 | 2/1984 | Toyomura ............................ | 381/51 |

*Primary Examiner*—Lee S. Cohen
*Assistant Examiner*—Angela D. Sykes
*Attorney, Agent, or Firm*—Birch, Stewart, Kolasch & Birch

[57] ABSTRACT

An electronic sphygmomanometer includes a digital display for visually displaying a systolic pressure and a diastolic pressure, and a synthetic speech generation system for audibly announcing the systolic pressure and the diastolic pressure. Switches are provided for selectively enabling the digital display and the synthetic speech generation system. Earphones are connectable to the electronic sphygmomanometer to hear the audible output of the systolic pressure and the diastolic pressure where neither the synthetic speech generation system nor the digital display is enabled.

8 Claims, 4 Drawing Figures

DISPLAY INHIBITION IN AN ELECTRONIC SPHYGMOMANOMETER

BACKGROUND OF THE INVENTION

The present invention relates to a blood pressure measuring instrument, i.e., a sphygmomanometer and, more particularly, to an electronic sphygmomanometer with a voice synthesizer for speaking patient's systolic and diastolic pressures.

Conventionally, systolic blood pressure and a diastolic blood pressure are measured using an inflatable occluding cuff which usually is wrapped about a patient's limb so as to close, or completely occlude, an artery. Typically, the occluding cuff is wrapped about the arm in juxtaposition to the brachial artery. When the cuff is inflated to a pressure which exceeds the patient's systolic pressure, so as to close this artery, blood is no longer capable of flowing therethrough. As the cuff is slowly deflated, a point is reached where the patient's systolic pressure exceeds the cuff pressure. Consequently, the artery opens for a short period during the patient's cardiac cycle. Once the blood pressure during this cardiac cycle falls below the cuff pressure, the artery once again is closed.

The pressure in the cuff which is equal to the maximum blood pressure during a cardiac cycle is, of course, the systolic pressure. It is known that when the blood pressure exceeds the actual cuff pressure, resulting in the opening of the artery, turbulence in the blood stream is accompanied by a sound which is the so-called Korotkoff sound. These Korotkoff sounds occur each time the artery is opened. Thus, as long as the cuff pressure exceeds the lowest, or diastolic, pressure in the cardiac cycle, the artery will be alternately opened and closed as the cardiac cycle pressure traverses the cuff pressure. When the cuff pressure falls below the lowest pressure point in the cardiac cycle, the artery will remain opened, and the Korotkoff sounds no longer will be produced. Consequently, by measuring the cuff pressure at the last Korotkoff sound, a close approximation is made of the patient's diastolic pressure.

In the conventional electronic sphygmomanometer, an operator must read the systolic and diastolic pressures visually displayed in a digital or analog display. This may produce an erroneous reading. Therefore, an electronic sphygmomanometer has been developed wherein the systolic pressure and the diastolic pressure are audibly output through the use of a synthetic speech system. The combination of the audible output and the visual display provides accurate recognition.

However, of great importance and which should be considered is the fact that the blood pressure of a patient may be greatly influenced by the patient's awareness of the visual display or the audible output of his or her pressure.

OBJECT AND SUMMARY OF THE INVENTION

Accordingly, an object of the present invention is to provide a novel control system for an electronic sphygmomanometer which audibly outputs the measured blood pressure through the use of a synthetic speech system.

Another object of the present invention is to provide an electronic sphygmomanometer which selectively displays or announces the measured blood pressure.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

To achieve the above objects, pursuant to an embodiment of the present invention, a first switch is provided for selectively enabling the synthetic speech output of the measured blood pressure via a speaker system. An earphone jack is connectable to the electronic sphygmomanometer for receiving the synthetic speech generation of the measured blood pressure when the first switch is turned off. A second switch is provided for selectively enabling the visual display of the measured blood pressure.

BRIEF DESCRIPTION OF THE DRAWINGS

The present invention will be better understood from the detailed description given hereinbelow and the accompanying drawings which are given by way of illustration only, and thus are not limitative of the present invention and wherein.

DESCRIPTION OF THE PREFERRED EMBODIMENTS

Figure 1:
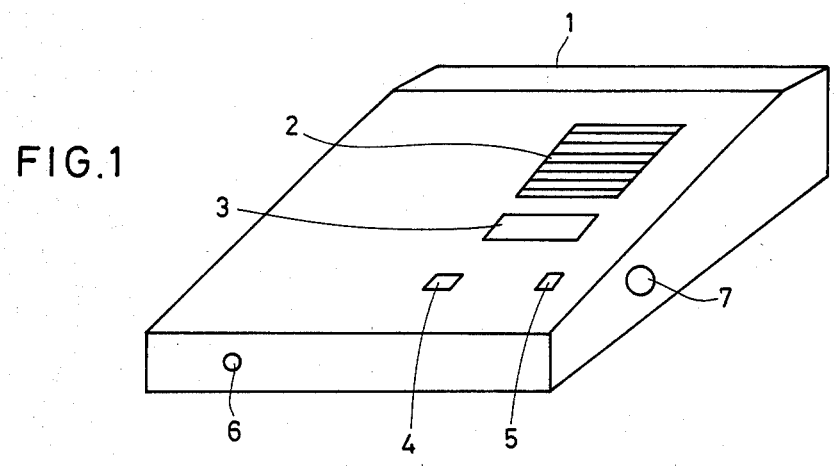
FIG. 1 is a perspective view of an embodiment of an electronic sphygmomanometer of the present invention.

FIG. 1 shows a perspective view of an electronic sphygmomanometer 1 according to the present invention. The sphygmomanometer 1 comprises a speaker 2, a digital display 3, a power switch 4, a repeat key 5, an earphone jack 6, and an adjuster knob 7.

Through the speaker 2, voice information representative of a measured blood pressure is output. The blood pressure, e.g., a systolic pressure and a diastolic pressure is displayed in the digital display 3. The power switch 4 is operated to control power to the sphygmomanometer 1.

The repeat key 5 is actuated to repeatedly speak the blood pressure of the systolic and diastolic pressures after the blood pressure has been measured and spoken. The speaker 2, the digital display 3, the power switch 4 and the repeat key 5 are disposed over the upper panel of the sphygmomanometer 1.

Earphones may be coupled to the earphone jack 6 disposed on the front panel of the sphygmomanometer 1. The adjuster knob 7 is rotated to adjust a pressure-reduction rate. The adjuster knob 7 is disposed on the right side of the sphygmomanometer 1. Although not shown, a connector terminal is provided to which a pressure hose is connected to supply pressurized air. The connector terminal is disposed on the left side of the sphygmomanometer 1. A display control switch is secured at the back of the body of the sphygmomanometer 1 to selectively activate the digital display 3.

Figure 2:
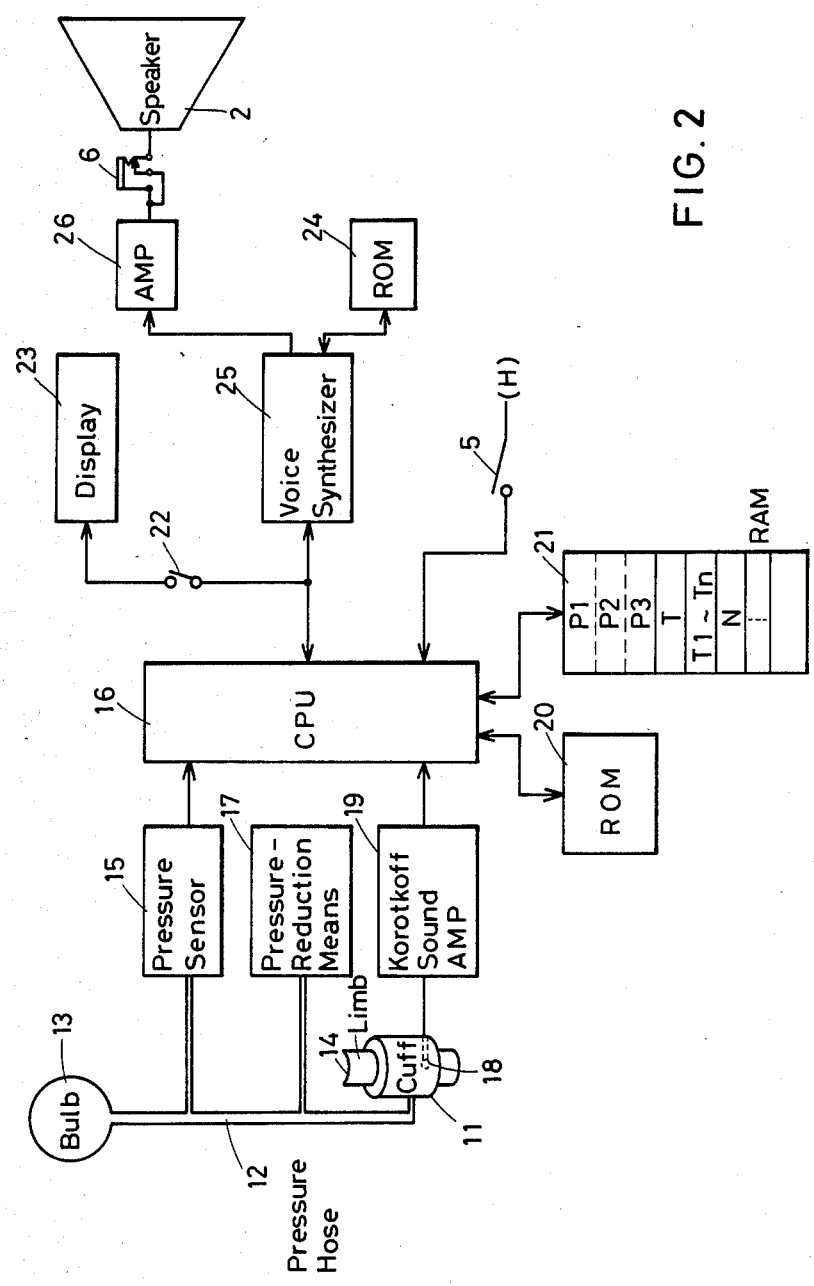
FIG. 2 is a block diagram of the electronic sphygmomanometer of FIG. 1.

FIG. 2 shows a block diagram of a circuit implemented within the sphygmomanometer 1.

As shown in FIG. 2 a device according to the invention includes an occluding cuff 11, applied to a patient's limb 14 a pressure hose 12, a bulb 13, a pressure sensor 15, a central processor unit 16, a pressure-reduction means 17, and a microphone 18.

The occluding cuff is adapted to be inflated by receiving a fluid, such as air, applied thereto by the pressure hose 12. The cuff 11 may be wrapped around the patient's limb 14 such as the upper arm to surround the brachial artery. Alternatively, the cuff may be wrapped around a patient wrist. Suitable fastening members, not shown, are used to maintain the cuff in a suitable position during inflation and deflation, and during pressure measurement.

The cuff 11 is manually inflated by squeezing the bulb 13. Fluid pulses are applied from the bulb 13 to the cuff 11 via the pressure hose 12. After inflation, the cuff 11 is adapted to be deflated.

The air pressure in the cuff 11 is communicated via the air connector to the pressure sensor 15, so that the pressure sensor transduces the air pressure in the cuff 11 to electric analog signals. The pressure sensor 15 comprises a bellows for lengthening and shrinking responsive to an applied pressure, an oscillator, and a means for changing oscillation frequency developed from the oscillator according to the movement of the bellows.

The analog signals developed from the pressure sensor 15 are applied to the central processor unit 16 so as to convert the analog signals into electrical digital signals representative of the cuff pressure.

The pressure-reduction means 17 is provided for reducing the cuff pressure, gradually. The means 17 comprises a needle valve for escaping the cuff pressure. A pressure-reduction rate provided by the means 17 is controlled by rotating the adjuster knob 7. The microphone 18 is provided within the cuff 11 for detecting the Korotkoff sounds. The Korotkoff sounds detected are entered into the central processor unit 16 via an amplifier 19. The microphone 18 is of a ceramic piezoelectric type.

The electronic sphygmomanometer 1 further includes a ROM 20, a RAM 21, a display control switch 22, a digital display 23, another ROM 24, and a voice synthesizer 25.

The CPU 16 receives the pressure output of the pressure sensor 15 to transduce the analog signals into the digital signals. The Korotkoff sound amplifier 19 amplifies the Korotkoff sounds detected by the microphone 18, so that the sounds amplified are inputted into the CPU 16.

Figure 3:
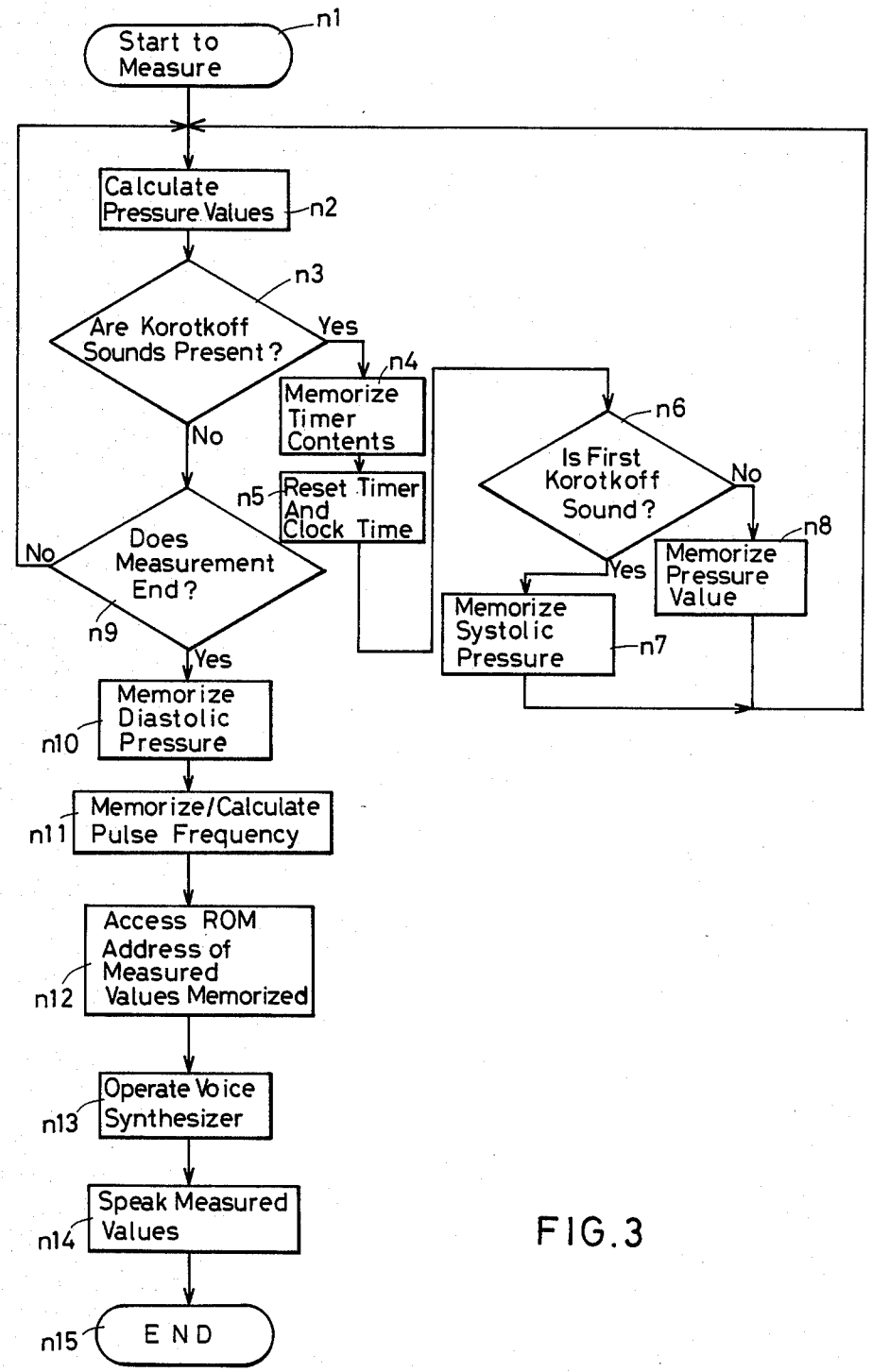
FIG. 3 is a flow chart for explaining an operational mode of the electronic sphygmomanometer of FIGS. 1 and 2.

The CPU 16 is responsive to the control by the ROM 20 for calculating the pressures on the basis of the outputs of the pressure sensor 15 and the Korotkoff sound amplifier 19. Further, the CPU 16 detects the systolic pressure, the diastolic pressure and the pulse frequency, so as to store these measured data in locations $P_1$ to $P_3$ and N of the RAM 21. The ROM 20 stores a program operated as shown in FIG. 3.

The CPU 16 sends the measured data as stored in the RAM 21 toward the digital display 23 (corresponding to the digital display 3 of FIG. 1) via the display control switch 22.

After the CPU 16 detects the measurement completion, it changes the measured data in the RAM 21 into addresses for voice information as stored in the ROM 24. The CPU 16 inputs the voice information addresses and the control signals into the voice synthesizer 25. Responsive to the voice information addresses and the control signals, the voice synthesizer 25 synthesizes speech output based on the voice information in the ROM 24.

After being amplified by an amplifier 26, the synthesized voice is spoken by the speaker 2. The earphone jack 6 is disposed between the amplifier 26 and the speaker 2 so that the speaker 2 is turned off when the earphone is inserted into the earphone jack 6.

FIG. 3 shows an operational mode of the electronic sphygmomanometer of FIGS. 1 and 2.

In operation, the cuff pressures during the inflation are detected by the pressure sensor 15 and the electrical analog signals are inputted into the CPU 16. The address information, for the ROM 24, corresponding to the pressures and the control signals are applied to the voice synthesizer 25, so that the synthesizer 25 makes the voice information. The voice information representative of the pressures during the inflation is spoken by the speaker 2.

Step $n_1$:

The operator inflates the cuff 11 until the cuff pressure exceeds an assumed systolic pressure by some value, e.g., about 30 mmHg, referring to the voice outputs of the pressures.

When the inflation is completed, the cuff 11 is deflated by operating the pressure-reduction means 17. The deflation operation is detected by the CPU 16 to start to measure the blood pressures.

Step $n_2$:

The pressures as detected by the pressure sensor 15 during the deflation are inputted into the CPU 16, for the CPU 16 to calculate the pressures from the digital signals.

Step $n_3$:

After the cuff inflation stops, the microphone 18 detects the Korotkoff sound which is to be amplified by the amplifier 19. The amplified sound is inputted into the CPU 16. The CPU 16 monitors the thus inputted Korotkoff sounds.

Step $n_4$:

By detecting the input of the Korotkoff sounds, the CPU 16 enables the clock contents of timer T in the RAM 21 to be stored in timer locations $T_1-T_n$ in the RAM 21.

Step $n_5$:

The clock contents of the timer T are reset and a next clocking operation of this timer T starts.

Step $n_6$:

The CPU 16 determines whether the inputtted Korotkoff sound is the first one or not.

Step $n_7$:

When the first Korotkoff sound is detected, the CPU 16 forwards the present cuff pressure toward a location $P_1$ in the RAM 21. The location $P_1$ memorizes it as the systolic pressure.

Step $n_8$:

When the Korotkoff sound is not the first one, the CPU 16 forwards the present cuff pressure toward a location $P_3$ in the RAM 21 for revising the value stored therein.

Step $n_2$ is reselected, so that the above steps are repeated, if necessary.

According to the above procedure, the timer T contains time intervals between the Korotkoff sounds. The time intervals in the timer T are subsequently stored in the locations $T_1-T_n$.

Step $n_9$:

When the CPU 16 detects no Korotkoff sounds being inputted in step $n_3$, step $n_9$ is selected to determine whether the pressure measurements are completed. More particularly, the CPU 16 determines whether the timer T contains a time more than a predetermined value, e.g., about 5 sec. When the time is less than this predetermined value, step $n_2$ is reselected. When the time is more than this predetermined value, the pressure measurement completion is detected to thereby select step $n_{10}$.

Step $n_{10}$:

A location $P_2$ in the RAM 21 stores a cuff pressure as stored in the location $P_3$ at the time when the last Korotkoff sound is detected, as the diastolic pressure.

Step $n_{11}$:

The pulse frequency is calculated, so that the pulse frequency is stored in the location N in the RAM 21. The CPU 16 calculates the pulse frequency from the time intervals of the Korotkoff sounds as stored in the locations $T_1$-$T_n$ in the RAM 21. For example, the pulse frequency is obtained by dividing 60 by a median value (sec.) of the data in the locations $T_1$-$T_n$.

Step $n_{12}$:

The CPU 16 extracts the systolic pressure, the diastolic pressure, and the pulse frequency from the locations $P_1$, $P_2$ and N in the RAM 21, respectively. The CPU 16 determines the address information, so that the ROM 24 generates the voice information corresponding to the systolic pressure, the diastolic pressure and the pulse frequency as extracted by the CPU 16. The voice information and the control signals are inputted into the voice synthesizer 25.

Step $n_{13}$:

Responsive to the control signals and the address information generated by the CPU 16, the voice synthesizer 25 synthesizes voice for the systolic pressure, the diastolic pressure and the pulse frequency, by extracting the voice information from the ROM 24.

Step $n_{14}$:

The speaker 2 is operated to speak the systolic pressure, the diastolic pressure and the pulse frequency, sequentially.

Step $n_{15}$:

The blood pressure measurement is completed.

As stated above, when the CPU 16 detects the pressure measurement completion in step $n_9$, steps $n_{10}$-$n_{14}$ are selected to speak the systolic pressure, the diastolic pressure and the pulse frequency.

The display control switch 22 is closed to forward the data for the systolic pressure, the diastolic pressure and the pulse frequency toward the digital display 23, so that they are displayed digitally in the display 23. When the display control switch 22 is opened, these data are not displayed in the digital display 23.

When the earphones are connected to the earphone jack 6, the speaker 2 is prevented from operating. When the operator uses the earphones to hear the systolic pressure, the diastolic pressure and the pulse frequency, the patient is prevented from hearing these measured data.

Figure 4:
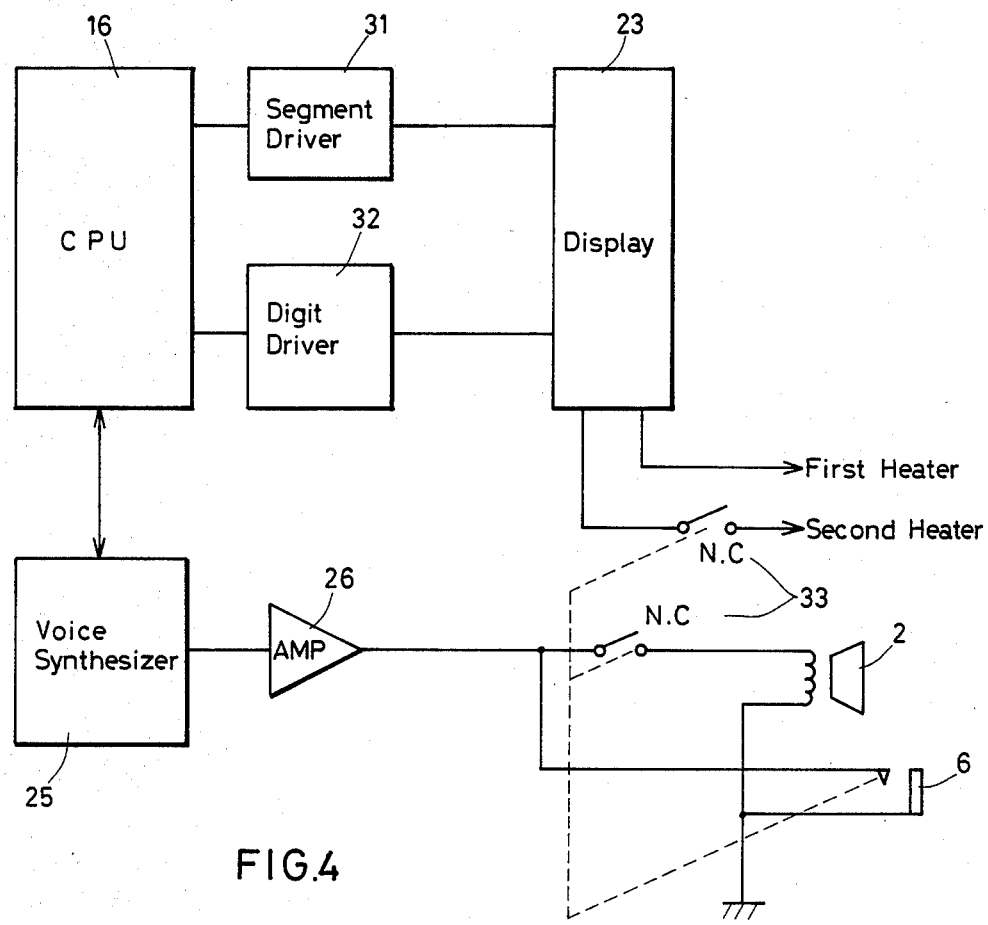
FIG. 4 is a block diagram of an essential part of another embodiment of an electronic sphygmomanometer of the present invention.

FIG. 4 shows an essential part of another embodiment of an electronic sphygmomanometer of the present invention. Like elements corresponding to those of FIG. 2 are indicated by like numerals.

The digital display 23 is made of a fluorescent display tube. A segment driver 31 and a digit driver 32 are disposed between the central processor unit 16 and the digital display 23 for enabling the digital display 23.

Correlation switches 33 are disposed in the heater circuit of the digital display 23 and the input side of the speaker 2. The correlation switches 33 are associated with the earphone jack 6 so that the correlation switches are turned off when the earphone plug is inserted into the earphone jack 6.

When the earphone plug is not inserted into the earphone jack 6, the correlation switches 33 are held in the ON state. Accordingly, the digital display 23 displays measured value, and the speaker 2 develops the synthetic speech of the measured value.

Contrarily, when the earphone plug is inserted into the earphone jack 6, the correlation switches 33 are turned off so that neither the digital display 23 nor the speaker 2 is activated.

The invention being thus described, it will be obvious that the same may be varied in many ways. Such variations are not to be regarded as a departure from the spirit and scope of the invention, and all such modifications are intended to be included within the scope of the following claims.

What is claimed is:

1. An electronic sphygmomanometer comprising:
   pressure detection means;
   determination means operatively connected to said pressure detection means for determining a person's systolic pressure and diastolic pressure;
   digital display means for visually displaying said systolic pressure and said diastolic pressure; and
   inhibition means for selectively preventing said person from receiving an indication of said systolic pressure and said diastolic pressure during detection thereof by inhibiting the operation of said digital display means.

2. An electronic sphygmomanometer comprising:
   pressure detection means for detecting a cuff pressure;
   Korotkoff sound detection means for detecting Korotkoff sounds;
   determination means for determining a person's systolic pressure and diastolic pressure in accordance with output signals derived from said pressure detection means and said Korotkoff sound detection means;
   memory means for temporarily storing digital data representing said systolic pressure and said diastolic pressure determined by said determination means;
   synthetic speech generation means for providing audible output of said digital data temporarily stored in said memory means; and
   means for preventing said person from receiving an indication of said data representing said systolic pressure and said diastolic pressure comprising inhibition means for selectively disabling said synthetic speech generation means.

3. The electronic sphygmomanometer of claim 2, wherein said synthetic speech generation means comprises:
   a voice synthesizer means for developing analog signals indicative of said digital data temporarily stored in said memory means;
   an amplifier means for amplifying said analog signals developed from said voice synthesizer means; and
   a speaker means for developing audible output in accordance with the amplified means signal derived from said amplifier.

4. The electronic sphygmomanometer of claim 3, wherein said inhibition means comprises:
a manual switch disposed between said amplifier means and said speaker means.

5. An electronic sphygmomanometer comprising:
pressure detection means for detecting a cuff pressure;
Korotkoff sound detection means for detecting Korotkoff sounds;
determination means for determining a person's systolic pressure and diastolic pressure in accordance with output signals derived from said pressure detection means and said Korotkoff sound detection means;
memory means for temporarily storing digital data representing said systolic pressure and said diastolic pressure determined by said determination means;
synthetic speech generation means for providing audible output of said digital data temporarily stored in said memory means;
display means for visually displaying said systolic pressure and said diastolic pressure in accordance with said digital data temporarily stored in said memory means;
first switching means for selectively enabling said synthetic speech generation means and for preventing said person from receiving an audible indication of said systolic pressure and diastolic pressure by disabling said synthetic speech generation means;
second switching means for selectively enabling said display means and for preventing said person from receiving a visual display of said systolic pressure and diastolic pressure by disabling said display means; and
earphone jack means for facilitating audible output through earphones in accordance with said digital data temporarily stored in said memory means.

6. The electronic sphygmomanometer of claim 5, wherein said synthetic speech generation means comprises:
a voice synthesizer means for developing analog signals indicative of said digital data temporarily stored in said memory means;
an amplifier means for amplifying said analog signals developed from said voice synthesizer means; and
a speaker means for developing audible output in accordance with the amplified means signal derived from said amplifier.

7. The electronic sphygmomanometer of claim 6, wherein said first switching means is disposed between said amplifier means and said speaker means.

8. The electronic sphygmomanometer of claim 7, wherein said earphone jack means is associated with said first and second switching means so that said first and second switching means are switched off thereby disabling both said display means and said synthetic speech generation means when an earphone plug is inserted into said earphone jack means.

* * * * *